United States Patent
Ishii et al.

(10) Patent No.: US 10,345,455 B2
(45) Date of Patent: Jul. 9, 2019

(54) RADIATION DETECTION APPARATUS, RADIATION IMAGING SYSTEM, AND METHOD OF MANUFACTURING RADIATION DETECTION APPARATUS

(71) Applicant: CANON KABUSHIKI KAISHA, Tokyo (JP)

(72) Inventors: Takamasa Ishii, Honjo (JP); Kota Nishibe, Kawasaki (JP); Tomohiro Hoshina, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/043,340

(22) Filed: Jul. 24, 2018

(65) Prior Publication Data

US 2019/0033470 A1 Jan. 31, 2019

(30) Foreign Application Priority Data

Jul. 31, 2017 (JP) .................. 2017-148201

(51) Int. Cl.
*A61B 6/00* (2006.01)
*G01T 1/20* (2006.01)
*G01T 1/166* (2006.01)
*G01T 1/202* (2006.01)

(52) U.S. Cl.
CPC .......... *G01T 1/2006* (2013.01); *A61B 6/4266* (2013.01); *A61B 6/464* (2013.01); *G01T 1/1663* (2013.01); *G01T 1/202* (2013.01)

(58) Field of Classification Search
CPC ...... G01T 1/2006; G01T 1/1663; G01T 1/202
See application file for complete search history.

(56) References Cited

U.S. PATENT DOCUMENTS

| 6,207,944 B1* | 3/2001 | Spartiotis .......... H01L 27/14601 250/208.1 |
| 6,273,606 B1* | 8/2001 | Dewaele ............. A61B 6/5241 378/174 |
| 6,403,964 B1* | 6/2002 | Kyyhkynen ........... H04N 5/379 250/370.09 |
| 7,223,981 B1* | 5/2007 | Capote ............. H01L 27/14634 250/370.13 |
| 7,381,965 B2 | 6/2008 | Ishii et al. |
| 7,473,903 B2* | 1/2009 | DeJule ................. G01T 1/2018 250/370.11 |
| 7,541,617 B2 | 6/2009 | Mochizuki et al. |

(Continued)

FOREIGN PATENT DOCUMENTS

JP 2012-027002 A 2/2012

*Primary Examiner* — David P Porta
*Assistant Examiner* — Djura Malevic
(74) *Attorney, Agent, or Firm* — Venable LLP

(57) ABSTRACT

A radiation detection apparatus includes a plurality of detection substrates on which photoelectrical conversion elements are arranged, a plate configured to support the plurality of detection substrates, a scintillator, and a plurality of bonding material members configured to bond the plurality of detection substrates and the scintillator. The plurality of bonding material members bond one-side surfaces of the plurality of detection substrates and a one-side surface of the scintillator, and the plurality of bonding material members are separated from each other and arranged so that outer edges of the plurality of bonding material members are not positioned between the plurality of detection substrates.

11 Claims, 3 Drawing Sheets

(56) References Cited

U.S. PATENT DOCUMENTS

| | | | |
|---|---|---|---|
| 7,622,719 B2 * | 11/2009 | Spahn | G01T 1/2018 250/370.11 |
| 7,629,564 B2 | 12/2009 | Mochizuki et al. | |
| 7,645,976 B2 | 1/2010 | Watanabe et al. | |
| 7,728,303 B2 * | 6/2010 | Mori | G01T 1/2018 250/370.01 |
| 7,750,422 B2 | 7/2010 | Watanabe et al. | |
| 7,812,313 B2 | 10/2010 | Mochizuki et al. | |
| 7,812,317 B2 | 10/2010 | Watanabe et al. | |
| 7,858,947 B2 | 12/2010 | Mochizuki et al. | |
| 7,923,695 B2 | 4/2011 | Ishii et al. | |
| 7,932,946 B2 | 4/2011 | Ishii et al. | |
| 8,067,743 B2 | 11/2011 | Ishii et al. | |
| 8,084,745 B2 | 12/2011 | Mochizuki et al. | |
| 8,154,641 B2 | 4/2012 | Nomura et al. | |
| 8,368,027 B2 | 2/2013 | Ishii et al. | |
| 8,440,975 B2 | 5/2013 | Inoue et al. | |
| 8,519,344 B2 | 8/2013 | Ishii et al. | |
| 8,653,463 B2 | 2/2014 | Sawada et al. | |
| 8,680,472 B2 | 3/2014 | Mochizuki et al. | |
| 8,957,383 B2 | 2/2015 | Sasaki et al. | |
| 9,081,104 B2 | 7/2015 | Sawada et al. | |
| 9,354,333 B2 | 5/2016 | Inoue et al. | |
| 9,366,767 B2 | 6/2016 | Inoue et al. | |
| 9,529,094 B2 * | 12/2016 | Ishii | G01T 1/2018 |
| 2006/0071172 A1 * | 4/2006 | Ertel | G01T 1/1644 250/370.11 |
| 2007/0272873 A1 * | 11/2007 | Jadrich | G01T 1/20 250/370.11 |
| 2009/0065703 A1 * | 3/2009 | Jadrich | G01T 1/2928 250/370.11 |
| 2010/0012846 A1 * | 1/2010 | Wang | G01T 1/1642 250/362 |
| 2010/0127178 A1 * | 5/2010 | Laurence | G01T 1/202 250/363.04 |
| 2011/0017916 A1 * | 1/2011 | Schulz | G01T 1/202 250/368 |
| 2013/0020493 A1 | 1/2013 | Ishii et al. | |
| 2013/0092840 A1 * | 4/2013 | Ohta | A61B 6/4283 250/361 R |
| 2013/0153775 A1 * | 6/2013 | Nomura | G01T 1/2006 250/366 |
| 2013/0187054 A1 | 7/2013 | Ishii et al. | |
| 2013/0221198 A1 | 8/2013 | Sawada et al. | |
| 2013/0341516 A1 * | 12/2013 | Ishida | G01T 1/2006 250/363.02 |
| 2014/0034836 A1 | 2/2014 | Takei et al. | |
| 2016/0097865 A1 | 4/2016 | Sasaki et al. | |
| 2016/0274250 A1 * | 9/2016 | Ishida | G01T 1/202 |

* cited by examiner

RADIATION DETECTION APPARATUS, RADIATION IMAGING SYSTEM, AND METHOD OF MANUFACTURING RADIATION DETECTION APPARATUS

BACKGROUND OF THE INVENTION

Field of the Invention

The present invention relates to a radiation detection apparatus that detects radiation, a radiation imaging system that uses the radiation detection apparatus, and a method of manufacturing the radiation detection apparatus.

Description of the Related Art

An indirect-type radiation detection apparatus includes a detection substrate on which photoelectric conversion elements are arranged in a matrix and a scintillator that converts radiation into light that can be sensed by the photoelectric conversion elements. Japanese Patent Laid-Open No. 2012-27002 discloses a radiation detection apparatus in which a plurality of detection substrates have been adhered to a scintillator by a continuous adhesive layer.

Since each member of the radiation detection apparatus according to Japanese Patent Laid-Open No. 2012-27002 can expand and contract due to temperature changes and vibrations that occur while the apparatus is used, the adhesive layer may peel off and become deformed. As a result, the shape of the adhesive layer which is positioned between the detection substrates may change. This change in the shape of the adhesive layer can influence the light propagation state from the scintillator to the detection substrates, and artifacts may be generated in an image signal obtained from the detection substrates.

SUMMARY OF THE INVENTION

The present invention has been made in consideration of the above situation, and provides a radiation detection apparatus in which the generation of artifacts is suppressed.

According to an aspect of the present invention, the present invention provides a radiation detection apparatus comprising a plurality of detection substrates on which photoelectrical conversion elements are arranged, a plate configured to support the plurality of detection substrates, a scintillator, and a plurality of bonding material members configured to bond the plurality of detection substrates and the scintillator, wherein the plurality of bonding material members bond one-side surfaces of the plurality of detection substrates and a one-side surface of the scintillator, and the plurality of bonding material members are separated from each other and arranged so that outer edges of the plurality of bonding material members are not positioned between the plurality of detection substrates.

Further features of the present invention will become apparent from the following description of exemplary embodiments with reference to the attached drawings.

DESCRIPTION OF THE EMBODIMENTS

Figure 1:
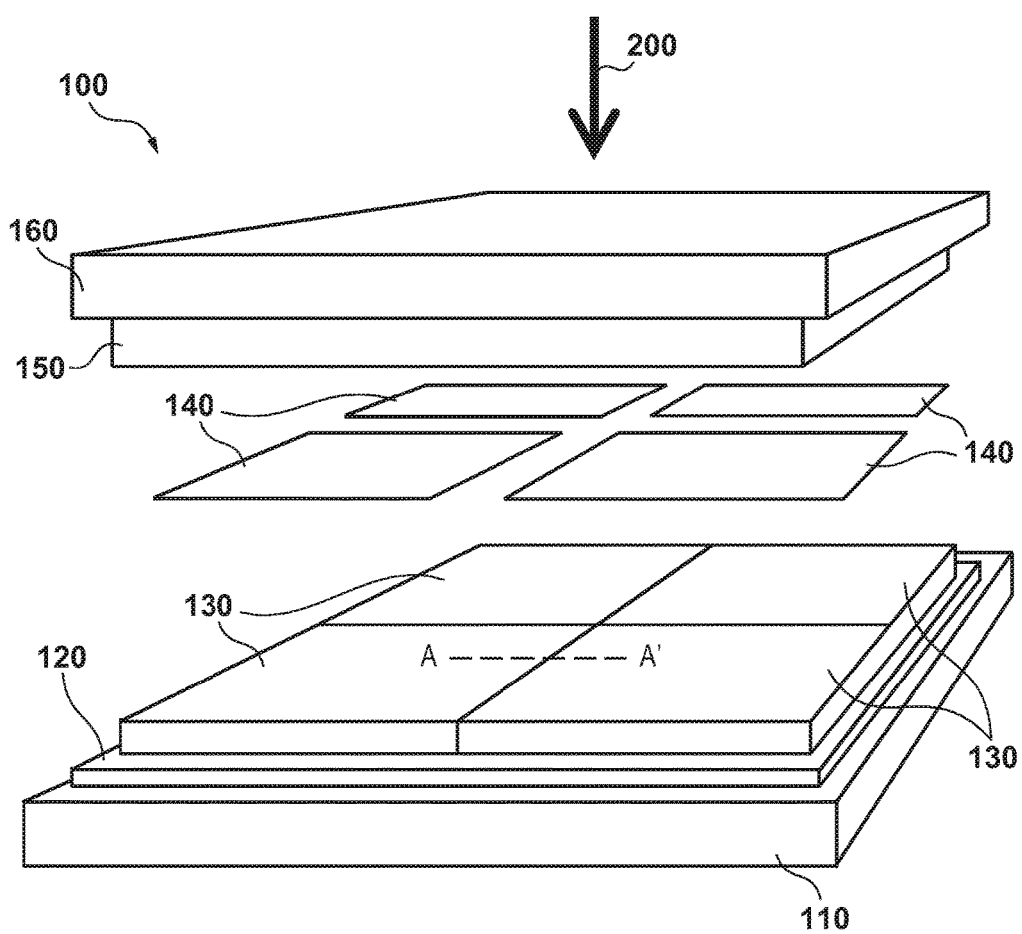
FIG. 1 is a perspective view of a radiation detection apparatus according to an embodiment of the present invention.

Embodiments of the present invention will be described in detail hereinafter with reference to the accompanying drawings. The same reference numerals denote the same components throughout the various embodiments, and a repetitive description thereof will be omitted. In the present invention, light includes visible light and infrared rays, and radiation includes X-rays, α-rays, β-rays, and γ-rays.

(First Embodiment)

An outline of a radiation detection apparatus 100 according to the first embodiment of the present invention will be described with reference to FIG. 1. The radiation detection apparatus 100 according to the embodiment includes a fixed plate 110, a plurality of detection substrates 130 which are supported by the fixed plate 110, a scintillator 150, and a protection plate 160 of the scintillator 150. For example, a glass plate is used as the fixed plate 110. Pixels including photoelectric conversion elements are arranged in a matrix on each detection substrate. An interval (to be referred to as a "pixel pitch" hereinafter) between pixels that are arranged on each detection substrate 130 can be set to 100 μm to 200 μm. The plurality of detection substrates 130 are supported by the fixed plate 110.

The scintillator 150 converts radiation into light of a wavelength which is detectable by the photoelectric conversion elements. The scintillator 150 has, for example, a columnar crystal structure made of cesium iodide doped with thallium. The scintillator 150 is formed, for example, by vapor deposition on the protection plate 160. Glass, amorphous carbon, CFRP, aluminum, titanium, and the like can be used as the protection plate 160. The scintillator 150 and the plurality of detection substrates 130 are bonded by a plurality of bonding material members 140.

Each photoelectric conversion element on the detection substrates 130 converts light generated by the scintillator 150 into an electric signal. As each photoelectric conversion element, a CMOS sensor using crystal silicon or a PIN type sensor or a MIS type sensor using amorphous silicon can be used. Alternatively, a known mechanism capable of detecting light and converting the detected light into an electrical signal can be used. In this embodiment, the plurality of detection substrates 130 are aligned and arranged so that large-screen imaging can be performed.

Figure 2:
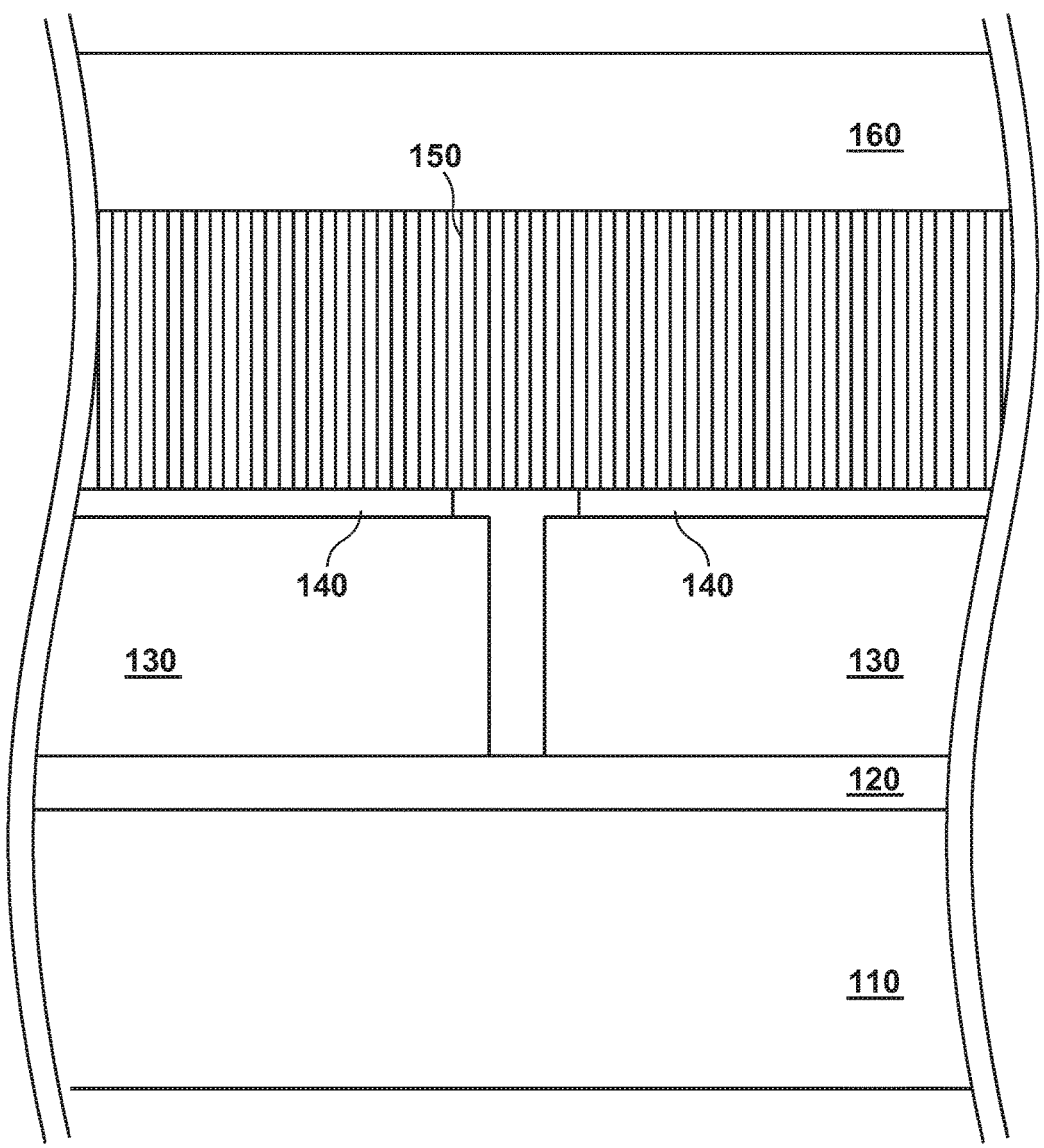
FIG. 2 is a sectional view of the radiation detection apparatus according to the embodiment of the present invention.

Although the scintillator 150 and the detection substrates 130 are drawn as though they are separated from each other in FIG. 1 for the sake of descriptive convenience, the members are actually layered and arranged in the manner as shown in FIG. 2. Additionally, in FIG. 1, depiction of parts unnecessary for the description of the present invention, such as a protective film for protecting an electrode and the scintillator 150 from humidity or the like, has been omitted. Although only four detection substrates 130 are shown in FIG. 1 for the sake of descriptive convenience, the number of the detection substrates 130 is not limited to this.

The radiation detection apparatus according to this embodiment operates as follows. Radiation emitted from the direction of an arrow 200 toward an object (not shown) is attenuated by the object and enters the scintillator 150. The scintillator 150 converts the radiation into light (for example, visible light) of a wavelength detectable by the photoelectric conversion elements. Light based on the radiation generated in the scintillator 150 enters the detection substrates 130 and is converted into an electric signal by each photoelectric conversion element. An image is generated by performing image processing on the electric signal.

The radiation detection apparatus 100 can also obtain a moving image by repetitively performing this operation.

A description of the radiation detection apparatus 100 will be given next with reference to the sectional view of FIG. 2. FIG. 2 is a sectional view of the radiation detection apparatus 100 taken along a line A-A' in FIG. 1. The plurality of detection substrates 130 are aligned and arranged by leaving an air gap between the plurality of detection substrates so as to form a flat surface to detect radiation, and the plurality of detection substrates are bonded to the fixed plate 110 via a fixing member 120. For example, glass, amorphous carbon, CFRP, aluminum, titanium, and the like can be used as the fixed plate 110. As the fixing member 120, for example, a sheet-like adhesive material member formed by arranging adhesive layers on the bottom and the top of a foam that has air gaps can be used. Since this type of a sheet-like adhesive material member has elasticity due to the air gaps in the foam, it has the effect of absorbing variation in the heights of the detection substrates 130 and flattening the imaging surface. Alternatively, a sheet-like, gel, or liquid adhesive material member including silicone resin, acrylic resin, epoxy resin, polyurethane resin, hot melt resin, and the like can be used.

The plurality of bonding material members 140 are arranged so as to correspond to the detection substrates 130. The bonding material members 140 are sandwiched between the one-side surfaces of the detection substrates 130 and the one-side surface of the scintillator 150, and bond the detection substrates 130 to the scintillator 150. The bonding material members 140 are arranged so as to be separated from each other. In the peripheral end portions of the detection substrates 130, the side surfaces of the plurality of detection substrates are arranged so that the detection substrates face each other, as shown in FIG. 2. The side surface of each detection substrate is called an end face. An air gap is formed between the end faces of the respective detection substrates 130. The outer edges of the bonding material members 140 are arranged so as not to be positioned between planes along the end faces. Similarly to the fixing member 120, for example, a sheet, a gel, or a liquid adhesive material including silicone resin, acrylic resin, epoxy resin, polyurethane resin, hot melt resin, and the like can be used as each bonding material member 140. Using a material with high light transmittance as the bonding material member 140 is advantageous in efficiently delivering light that has been generated in the scintillator 150 to each detection substrate 130. Since image clarity is reduced in accordance with an increase in thickness of the bonding material member 140, the thickness of each bonding material member 140 is set to 200 µm or less. Preferably, the thickness is set to 50 µm or less. However, a certain degree of thickness is required for each bonding material member 140 to maintain the bonding force between the scintillator 150 and the detection substrates 130. Therefore, the thickness of each bonding material member 140 is preferably set to 1 µm (inclusive) to 50 µm (inclusive).

As shown in FIG. 2, the bonding material members 140 are not arranged on the peripheral end portions of the plurality of detection substrates 130. It is preferable to arrange the adhesive material member, which is to serve as each bonding material member 140, at a position a predetermined distance away from the end face of the corresponding detection substrate 130 so the bonding material member 140 will not protrude from an area of the detection substrate 130, in consideration of the positioning accuracy at the time of the manufacture. When the detection substrates 130 and the scintillator 150 are to be bonded by the bonding material members 140, a portion sandwiched by the detection substrates 130 and the scintillator 150 can be bonded with sufficient strength by the bonding material members 140. However, even in the portion sandwiched by the detection substrates 130 and the scintillator 150, the strength of the outer edge portions of the bonding material members 140 decreases, the bonding material members 140 can easily peel off or become deformed. Hence, from the viewpoint of strength, the outer edge of a region occupied by each bonding material member 140, which is sandwiched by and bonds a corresponding detection substrate 130 and the scintillator 150, is arranged at an inside position away from the end face of the detection substrate 130 by a predetermined distance. In other words, a region occupied by the bonding material member 140 is arranged so that it is contained within a region occupied by the corresponding detection substrate 130. Hence, the area occupied by each bonding material member 140 that is provided between a corresponding detection substrate 130 and the scintillator 150 is smaller than the area of a surface of the corresponding detection substrate 130.

By arranging each bonding material member 140 at an inside position from the end face of the corresponding detection substrate 130, it is possible to suppress the peeling or the deformation of the bonding material member 140 in the peripheral portions of the detection substrate 130 even when a temperature change or a vibration occurs. As a result, the generation of image artifacts is suppressed. The distance from the end face of each detection substrate 130 to the outer edge of the corresponding bonding material member 140 is preferably set to be equal to or more than at least the thickness of each bonding material member 140 provided between the scintillator 150 and the corresponding detection substrates 130.

On the other hand, the detection substrates 130 and the scintillator 150 will peel off more easily if the distance from the end face of each detection substrate 130 to the outer edge of the corresponding bonding material member 140 is long. Additionally, if a large air gap is formed between adjacent bonding material members 140, it can influence the light that is to enter a pixel. Hence, in consideration of the pixel pitch, the distance between the outer edges of adjacent bonding material members 140 that face each other is preferably set to be equal to or smaller than the pixel pitch, that is, preferably 100 µm or less.

To obtain an image signal advantageously, it is also preferable to set a small interval between adjacent detection substrates 130. An image loss may unwantedly occur if a large interval is set. Thus, in consideration of the pixel pitch of the detection substrates 130, this interval is preferably set to be equal to or smaller than the pixel pitch, that is, preferably 100 µm or less.

An example of a manufacturing method of the radiation detection apparatus 100 according to the embodiment of the present invention will be described next. First, the plurality of detection substrates 130 which are supported by the fixed plate 110 are prepared. For example, the preparation is performed as follows. An adhesive material member which is to serve as the fixing member 120 is adhered on the fixed plate 110. In a case in which the adhesive material member is a sheet-like adhesive material member, the sheet-like adhesive material member is placed on the fixed plate 110 and pressure-pasted by a roller. This can prevent the mixture of air bubbles between the fixed plate 110 and the adhesive material member. Next, the plurality of detection substrates 130 are sequentially arranged at predetermined positions on the adhesive material member, and the fixed plate 110 and the detection substrates 130 are bonded by adhesion.

On the other hand, adhesive material members that are to serve as the bonding material members 140 are adhered on the scintillator 150 formed on the protection plate 160. Each adhesive material member is arranged on the scintillator 150 at a position where a corresponding detection substrate 130 is to be arranged. In a case in which each adhesive material member is made of a sheet-like adhesive material, it is preferable to paste the adhesive material member to the scintillator 150 by pressing the adhesive material member by a roller. This can prevent the mixture of air bubbles from between the scintillator 150 and each adhesive material member, and also allow the adhesive material member to adhere closely to the unevenness of the surface of the scintillator 150. Hence, the adhesive material members are preferably adhered to the scintillator 150 before the adhesion of the detection substrates 130. In order to suppress the decrease in sensitivity and resolution of the radiation detection apparatus 100, the adhesive material member is preferably made of a transparent and thin material.

Caution against the mixture of a foreign substance is required in the process in which each adhesive material member is adhered to the scintillator 150. The sheet-like adhesive material member may be separated into a plurality of members and be easily bendable. Since the use of separated sheet-like members allows each adhesive material member to be pasted in accordance with the shape of the scintillator 150 at the time of pasting, the adhesiveness between the adhesive material members and the scintillator 150 is improved.

The following method may also reduce the mixture of a foreign substance. A single thin transparent sheet is prepared. This transparent sheet is used as a support sheet for supporting the plurality of sheet-like adhesive material members. The plurality of sheet-like adhesive material members are arranged on the support sheet. At this time, the plurality of adhesive material members are arranged at the positions on the support sheet that correspond to the positions where the plurality of detection substrates 130 are to be arranged. The surface on the opposite side to the surface on which the adhesive material members are arranged on the support sheet is pasted onto the scintillator 150. The time taken to arrange the adhesive material members onto the scintillator 150 can be shortened by this method than the method of arranging the plurality of sheet-like adhesive material members onto the scintillator 150 sheet by sheet. As a result, the mixture of a foreign substance between the scintillator 150 and the bonding material members 140 can be reduced.

Finally, the detection substrates 130 supported by the fixed plate 110 and the scintillator 150 are pasted by the adhesive material members. Each of the adhesive material members becomes the bonding material member 140 that is to bond the surface of the corresponding one of the plurality of detection substrates 130 and the scintillator 150.

The above-described manufacturing method is merely an example, and the manufacturing method of the radiation detection apparatus is not limited to this. It is preferable to select a suitable manufacturing method in accordance with the properties of the adhesive material. For example, the adhesive material members may be arranged individually on the one-side surfaces of the plurality of detection substrates 130 in advance, and the detection substrates 130 may be adhered and bonded with the scintillator 150 after the detection substrates 130 have been supported by the fixed plate 110. Alternatively, detection substrates that are supported by the fixed plate 110 may be prepared, the adhesive material member may be arranged on each of the detection substrates 130, and the detection substrates 130 and the scintillator 150 may be bonded by the adhesive material members.

In this embodiment, each of the plurality of detection substrates 130 is individually bonded to the scintillator 150 by a corresponding one of the plurality of the bonding material members 140. At this time, to prevent each bonding material member 140 from protruding from the corresponding detection substrate 130, the adhesive material member which is to serve as the bonding material member 140 is not arranged on the peripheral end portions of the detection substrate 130. The areas and the pasting positions of the respective adhesive material members are adjusted so that the bonding material members 140 will not be present in the air gap portions between adjacent detection substrates 130 of the plurality of detection substrates 130. In other words, each bonding material member 140 bonds the corresponding detection substrate 130 and the scintillator 150 by being arranged inside the region where the detection substrate 130 and the scintillator 150 overlap. Peeling and deformation of the bonding material members 140 hardly occur since the bonding material members 140 are sandwiched between the detection substrates 130 and the scintillator 150 and the bonding material member 140 is arranged inside the region where the detection substrate 130 and the scintillator 150 overlap.

As described above, the present invention can provide the radiation detection apparatus 100 in which generation of artifacts by the deformation of the bonding material members 140 that can occur near the peripheral portions of the plurality of detection substrates 130 is suppressed.

(Second Embodiment)

Figure 3:
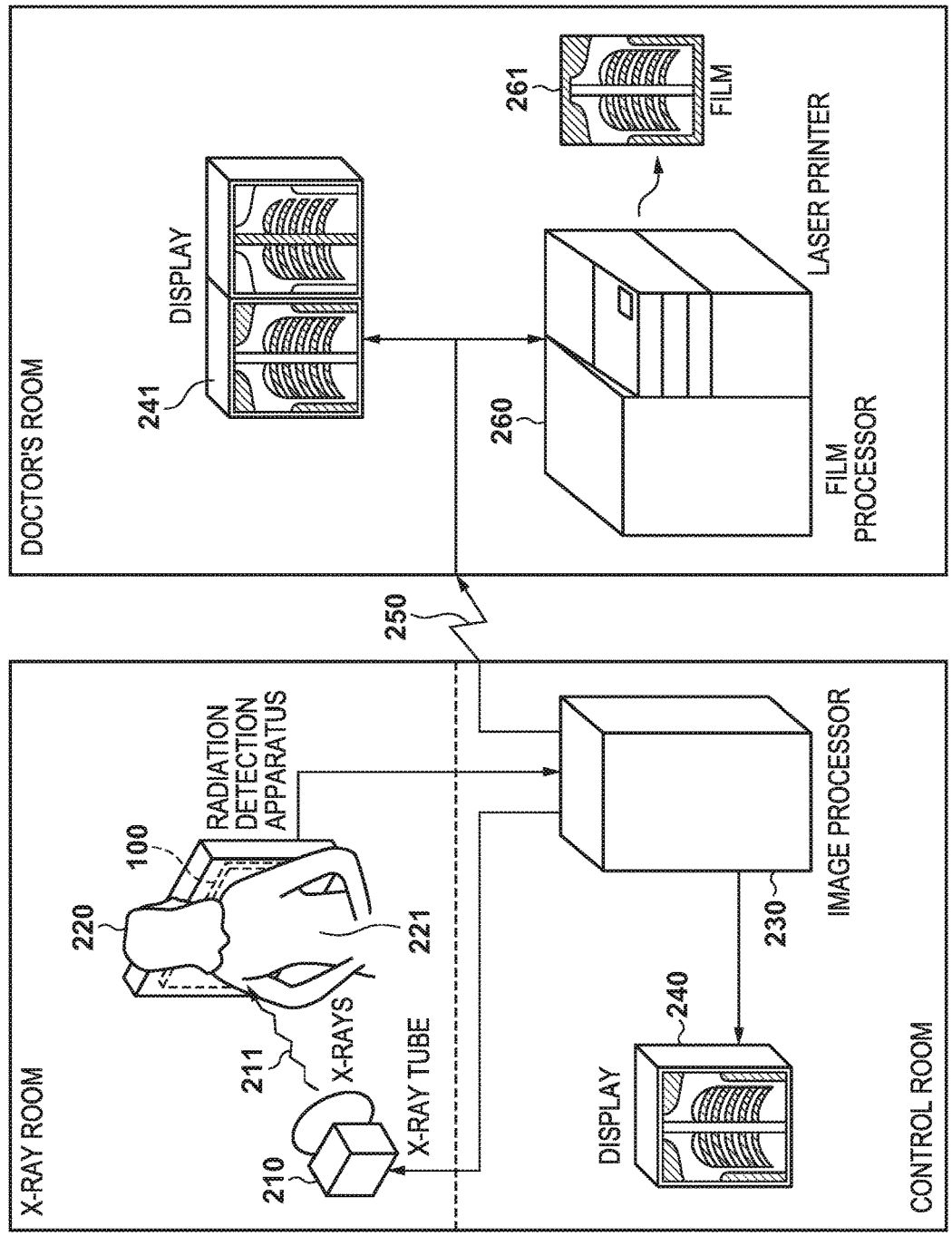
FIG. 3 is a conceptual view of a radiation detection system using a radiation detection apparatus according to the present invention.

FIG. 3 is a conceptual view of an X-ray diagnostic system (radiation imaging system) using a radiation detection apparatus according to the present invention. X-rays 211 as radiation generated by an X-ray tube 210 (radiation source) are transmitted through a chest region 221 of a patient or a subject 220, and enter a radiation detection apparatus 100 according to the present invention that includes a scintillator 150. The incident X-rays include in-vivo information of the subject 220. The scintillator 150 generates light corresponding to the incident X-rays, and an electrical signal is obtained by photoelectrically converting the generated light. The electrical signal is converted into a digital signal, image processing by an image processor 230 that operates as a signal processing unit, and can be observed by a display 240 which is a display unit in a control room. Note that the radiation imaging system includes at least the radiation detection apparatus and the signal processing unit that processes the signals from the radiation detection apparatus.

This information can be transferred to a remote location through a transmission processing unit such as a telephone line 250, be displayed in a display 241 which serves as a display unit in a doctor's room in separate place, or be stored in a recording unit such as an optical disk. This allows a doctor in a remote location to make a diagnosis. The information can also be recorded in a film 261 which serves as a recording medium by a film processor 260 which serves as a recording unit.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-148201, filed Jul. 31, 2017, which is hereby incorporated by reference herein in its entirety.

What is claimed is:

1. A radiation detection apparatus comprising:
a plurality of detection substrates on which photoelectrical conversion elements are arranged;
a plate configured to support the plurality of detection substrates;
a scintillator; and
a plurality of bonding material members, each of the bonding material members being configured to bond the scintillator and one detection substrate, wherein
the plurality of detection substrates are sandwiched between the plate and the scintillator,
each of the plurality of bonding material members is sandwiched between the scintillator and a detection substrate, and
the bonding material members are separated from each other such that outer edges of the bonding material members are not positioned between adjacently arranged detection substrates.

2. The apparatus according to claim 1, wherein the outer edges of each of the plurality of bonding material members are arranged separated from the end faces of each of the plurality of the detection substrates and at inside positions of the detection substrates.

3. The apparatus according to claim 1, wherein a distance between the outer edge of each of the plurality of bonding material members and the end face of a corresponding one of the plurality of the detection substrate is not less than the thickness of the bonding material member.

4. The apparatus according to claim 1, further comprising an air gap between adjacently arranged bonding material members.

5. The apparatus according to claim 1, wherein the plurality of bonding material members are sheet-like members.

6. The apparatus according to claim 5, wherein the sheet-like bonding material members are formed from a plurality of separated members.

7. The apparatus according to claim 1, wherein a distance between adjacently arranged plurality of detection substrates is not more than a pixel pitch of pixels arranged on the plurality of detection substrates.

8. A radiation imaging system comprising:
the radiation detection apparatus defined in claim 1; and
a signal processing unit configured to process a signal obtained by the radiation detection apparatus.

9. The apparatus according to claim 1, wherein each region in which a bonding material member is bonded to its corresponding detection substrate is included within a region of the corresponding detection substrate.

10. A method of manufacturing a radiation detection apparatus, the method comprising:
preparing a plurality of detection substrates supported by a plate; and
bonding each of the detection substrates to a scintillator using a plurality of bonding material members that are separated from each other, wherein
in the bonding, the plurality of detection substrates are sandwiched between the plate and the scintillator,
when each of the plurality of detection substrates are bonded to the scintillator, each of the plurality of bonding material members is sandwiched between a detection substrate and the scintillator, and
the bonding material members are separated from each other such that outer edges of the bonding material members are not positioned between adjacently arranged detection substrates.

11. The method according to claim 10, wherein the plurality of bonding material members are sheet-like members.

* * * * *